United States Patent [19]

Shalaby et al.

[11] 4,130,639

[45] Dec. 19, 1978

[54] ABSORBABLE PHARMACEUTICAL COMPOSITIONS BASED ON ISOMORPHIC COPOLYOXALATES

[75] Inventors: Shalaby W. Shalaby, Long Valley; Dennis D. Jamiolkowski, Paterson, both of N.J.

[73] Assignee: Ethicon, Inc., Somerville, N.J.

[21] Appl. No.: 837,060

[22] Filed: Sep. 28, 1977

[51] Int. Cl.$^2$ ...................... A61K 31/74; A61K 31/56
[52] U.S. Cl. .................................... 424/78; 424/238; 424/242; 424/243
[58] Field of Search ................................. 424/78, 238

[56] References Cited

U.S. PATENT DOCUMENTS 3,997,512  12/1976  Casey ........................................ 424/78

OTHER PUBLICATIONS

Chem. Abst. 9th col. Index – vol. 76–85, (1972–1976), p. 15124cs.

*Primary Examiner*—Sam Rosen
*Attorney, Agent, or Firm*—Wayne R. Eberhardt

[57] ABSTRACT

Absorbable copolyoxalate polymers having isomorphic sequences are formulated with drugs and introduced into the body to provide a slow, sustained release of the drug over an extended period of time in accordance with the rate of absorption of the polymer. The copolyoxalate polymers are derived from mixtures of cyclic and linear diols, each having the same number of carbon atoms. The polymers are biodegradable in animal tissue and absorb with minimal adverse tissue reaction.

15 Claims, No Drawings

ABSORBABLE PHARMACEUTICAL COMPOSITIONS BASED ON ISOMORPHIC COPOLYOXALATES

BACKGROUND OF THE INVENTION

1. Field of the Invention

This invention relates to novel polymer-drug compounds and their use in providing sustained release drug delivery to human and other warm-blooded animals. The polymer-drug compounds provide a mechanism whereby the rate of release and availability of the drug may be regulated so that the quantity of a drug which is released at a particular time or at a particular site is relatively constant and uniform over extended periods of time.

2. Description of Prior Art

Drugs are conventionally administered orally or via injection, often at a site remote from the target. Over a relatively short period of time, the drug diffuses into the circulation system of the patient and is distributed to the various organs, at least one of which is the intended target for the drug. The action of the drug on organs other than the target may result in undesirable side effects. Finally, the drug is metabolized or otherwise irreversibly removed from the organism by excretion or chemical deactivation.

When drugs are delivered orally or by injection, the level and duration of availability of the drug cannot be controlled independently; only the size and frequency of the dose can be manipulated. Typically, there is an initially high concentration of available drug at the site of injection or in the circulatory system which then decreases gradually as the drug is distributed and consumed within the body of the patient.

In controlled sustained delivery, a formulation of the drug and a carrier is administered to the patient by injection or implantation. The carrier forms a drug reservoir that protects the stored drug from extraneous removal mechanisms and releases the drug to the biological reservoir at a predetermined rate. Controlled sustained delivery of a drug prevents undesirable peaking of blood levels and makes the drug available at an optimum and uniform concentration over an extended period of time. Only the released drug is subject to removal via metabolism and excretion.

U.S. Pat. Nos. 3,773,919, 3,755,558, and 3,997,512 describe formulations of various polyactides, polyglycolides and copolymers of glycolide and lactide with some well-known drugs in order to achieve slow release of the drugs when implanted or applied topically to humans. These compositions are designed to release the drug over an extended period of time as the polymer of the mixture is slowly absorbed in the system. The polymer itself is nonreactive to body tissue and degrades into harmless products which are metabolized or excreted by the host body.

We have discovered that copolyoxalate polymers having isomorphic sequences are also absorbed slowly in animal tissue without significant adverse tissue reaction.

The preparation of polyoxalate polymers is described in the art. Carothers et al, J. Amer. Chem. Soc. 52, 3292 (1930), for example, describes the ester interchange reaction of diols such as ethylene glycol, 1,3-propanediol, or 1,4-butanediol with diethyl oxalate to yield a mixture of monomer, soluble polymer and insoluble polymer. The reaction of oxalic acid and an alkylene glycol to form polyester resins is described in U.S. Pat. No. 2,111,762, while the preparation of polyesters of fiber-forming quality from dicarboxylic acids and diols is described in U.S. Pat. No. 2,952,652. The reaction of ethylene glycol with oxalic acid to form fiber-forming polymer was described recently in J. Polym. Sci., Polym. Chem. Ed. 15, 1855 (1977). Isomorphic polymers including polyester copolymers have been discussed in "Isomorphism in Synthetic Macromolecular Systems", G. Allegra and I. W. Bassi, Adv. Polym. Sci. 6, 549 (1969). The particular isomorphic copolyoxalates of the present invention, however, have not previously been known, nor has their use in the preparation of sustained release drug compositions been previously suggested.

SUMMARY

Pharmaceutical depot compositions for parenteral administration of effective amounts of drugs over an extended period of time comprise mixtures and combinations of one or more drugs with absorbable, crystalline isomorphic polyoxalate polymers. The polymers are prepared by reacting mixtures of cyclic and linear diols with dialkyl oxalate, preferably in the presence of an inorganic or organometallic catalyst. The diols comprising the reaction mixture have the same carbon chain length separation between terminal OH groups of 6 or 8 carbon atoms. The cyclic diol may be trans 1,4-cyclohexane dialkanol or p-phenylene dialkanol and comprises from about 5 to 95 mole percent, and preferably from 35 to 80 mole percent of the total diol reactant.

The polyoxalate polymers and drugs are utilized as physical mixtures or as chemically bonded compounds. The polymer-drug composition may be administered to the patient by implantation as a solid pellet, by injection as a suspension in a biologically acceptable fluid, or by other convenient means.

DESCRIPTION OF THE INVENTION

The formulations of this invention are absorbable, nonirritating pharmaceutical compositions consisting of one or more drugs intimately mixed with or chemically bonded to an absorbable copolyoxalate polymer. When implanted in an animal system, effective amounts of the drug are released at a predetermined rate over an extended period of time as the polymer is absorbed in the system. The invention is of particular value for drugs that require prolonged administration as, for example, certain fertility-control drugs or hormones used for hormone-replacement therapy.

The novel formulations of the present invention permit the continuous release of drugs over an extended period of time from the sites of parenteral administration and minimize the frequency and thus the discomfort and inconvenience associated with conventional injection formulations. The poly(alkylene oxalate) polymers undergo biodegradation in the body into products which are nonreactive toward body tissue, and can be designed, by controlling molecular weight and composition, to undergo hydrolysis and release drug from the depot at a desired rate.

The Drug

The term "drug" is intended in its broadest sense as defined in the Federal Food, Drug and Cosmetic Act, Section 201(2)g:

(1) articles recognized in the official *United States Pharmacopoeia*, official *Homeopathic Pharmaco-* poeia of the United States, or official National Formulary, or any supplement of any of them; and (2) articles intended for use in the diagnosis, cure, mitigation, treatment, or prevention of disease in man or other animals; and (3) articles (other than food) intended to affect the structure or any function of the body of man or other animals; and (4) articles intended for use as a component of any article specified in clauses 1, 2 or 3; but does not include devices or their components, parts, or accessories.

Classes of drug which may be specifically mentioned include agents affecting the central nervous system, e.g., narcotics, such as, for example, morphine; narcotic antagonists, such as naloxone; antipsychotic agents, such as chlorpromazine and molindone; antianxiety agents, such as sodium pentobarbital; antidepressants, such as imipramine hydrochloride; stimulants, such as methyl phenadate and nikethamide; hallucinogens; analgesics, such as numorphan, meperidine, and morphine; and anorexigenic agents.

Other classes are pharmacodynamic agents, e.g., antihypertensive agents as reserpine, and chlorisondamine chloride, and antianginal agents, such as papaverine, and drugs for therapy of pulmonary disorders, such as theophylline ethylenediamine salt and epinephrine. Additional classes are chemotherapeutic agents, e.g., antiviral; antiparasitic, such as emetine hydrochloride and stibophen; antifungal agents, such as cycloheximide; and antineoplastic agents, such as triethylene thiophosphoramide; agents affecting metabolic diseases and endocrine functions, e.g., prostaglandins; atherosclerosins, such as heparin; steroids and biologically related compounds; polypeptides, such as bacitracin, polymixin B sulfate, and sodium colistimethate; natural and synthetic hormones, such as estradiol dipropionate, progesterone, and hydroxy progesterone caproate; steroid and nonsteroidal anti-inflammatory agents, such as gold sodium thiomalate and hydrocortisone sodium succinate; and agents affecting thrombosis, such as crystalline trypsin; vitamins, such as vitamin $B_{12}$; anti-epilepsy agents, such as phenobarbital; and the like. It should be understood that the specific drugs mentioned by name are illustrative and not limitative.

Endocrine agents comprise a particularly useful class of compounds in this invention and can be defined either as natural hormones or as synthetic drugs that to some extent act like, or antagonize, natural hormones. Endocrine agents include, but are not limited to, both steroids and nonsteroids that function as fertility-control agents; progestogens, estrogens, androgens, antiandrogens, corticoids, anabolic agents, and anti-inflammatory agents.

Examples of specific endocrine agents that can be used in the formulations of the invention are set forth in U.S. Pat. No. 3,773,919, particularly Columns 3 to 7, which patent is incorporated herein in its entirety by reference.

The Absorbable Polymer

Polymers of the present invention are comprised of isomorphic units of cyclic and linear oxalates and have the general formula

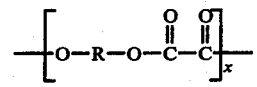

wherein each R is $$-(CH_2)_n-A-(CH_2)_n- \quad\quad I$$

or $$-(CH_2)_{4+2n} \quad\quad II$$

with from about 5 to 95 mole percent, and preferably from about 40 to 75 mole percent of R groups being I; A is trans 1,4-cyclohexylene or p-phenylene, n is 1 or 2 and is the same for I and II, and x is the degree of polymerization resulting in a polymer having a molecular weight which corresponds to a $\eta$inh of at least 0.2 determined at 25° C. on a 0.1 g/dl solution of polymer in chloroform or hexafluoroisopropanol.

Polymers of the present invention are conveniently prepared by an ester interchange reaction between the aforedescribed mixture of diols and a lower ester of oxalic acid, preferably in the presence of an ester interchange catalyst. The preferred ester of oxalic acid is diethyl oxalate. The ester interchange is most preferably conducted in two stages wherein the reactants are first heated with stirring under a nitrogen atmosphere to form a prepolymer with the removal of ethanol, followed by postpolymerization under heat and reduced pressure to obtain a final polymer of the desired molecular weight. Polymers with low or moderate degrees of polymerization are postpolymerized in the liquid state or as finely divided solid particles, depending on their melting temperature range.

As a rule, randomly constructed copolyester chains based on almost equal amounts of comonomer sequences are generally found to be noncrystalline. Contrary to this general rule, the isomorphic copolyesters of the present invention display a surprisingly high level of crystallinity of about 45 percent in a 50/50 copolyester. The polymers of the present invention are also unusual in that all copolymers through the entire composition range of from 5 to 95 percent of each isomorphic comonomer demonstrate levels of crystallinity comparable to those encountered in the parent homopolymers; namely, between about 30 and 50 percent depending on the thermal history.

The preparation of high molecular weight isomorphic polyoxalates is further illustrated by the following examples where all percentages are on a molar basis unless otherwise noted. The following analytical methods were used to obtain the data reported in the examples. Inherent viscosity ($\eta$inh) of polymer was determined at 25° C. on a 0.1 g/dl solution of polymer in chloroform or hexafluoroisopropanol (HFIP) as specified. A DuPont 990 DSC apparatus was used to determine the melting temperatures ($T_m$) of polymer in nitrogen, using about a 4 mg sample and a heating rate of 10 or 20° C./min as specified. Crystallinity was determined by the method of Hermans and Weidinger and the diffractometer patterns were resolved with a DuPont 310 curve analyzer.

In vitro hydrolysis of polymer discs (about 1.2 g, 2.2 cm diameter) and monofilaments (8-25 mil) were conducted in a phosphate buffer of pH 7.25 at 37° C.

In vivo absorption (muscle) was demonstrated by melt extruding the polymer into filaments and implanting two 2 cm segments of a filament into the left gluteal muscles of female Long-Evans' rats. The implant sites were recovered after periods of 60, 90, and 120 and 180 days and examined microscopically to determine the extent of absorption. In vivo absorption (subcutaneous) is a nonhistological technique in which continuous observation of the biological degradation of segments of the filament were made by implanting two filaments, 2 cm long, into the abdominal subcutis of young female rats. The implants are readily visible when the skin is wetted with propylene glycol and extent of absorption can be determined by subjective visual examination.

EXAMPLES

General Polymerization Procedure

Diethyl oxalate was heated with the selected diols in a stirred reactor using a stannous alkanoate or an organic titanate as a catalyst. The reaction was conducted under a nitrogen atmosphere at suitable temperatures until a substantial portion of the calculated amount of ethanol was obtained. Postpolymerization of the resulting prepolymer was then continued under reduced pressure using a suitable heating scheme. At the end of the postpolymerization period, the molten polymer was allowed to cool slowly at room temperature, isolated, ground and dried at 25° C. to 80° C. (depending on the polymer $T_m$) in vacuo for at least one day. Alternatively, the prepolymer can be postpolymerized partially in the liquid state, cooled, and then postpolymerized further in the solid state as finely divided particles. Detailed experimental conditions for the preparation of representative samples of isomorphic polyoxalates and important properties of the resulting polymers are presented below.

EXAMPLE I

95/5 Poly(trans 1,4-cyclohexylenedicarbinyl-cohexamethylene oxalate)

Distilled diethyl oxalate (19.0 g, 0.130 mole), recrystallized trans 1,4-cyclohexanedimethanol (19.8 g, 0.137 mole), 1,6-hexanediol (0.856 g, 0.00724 mole) and stannous octoate (0.33 M in toluene; 0.080 ml, 0.026 mmole) were added under dry and oxygen-free conditions to a glass reactor equipped for magnetic stirring. The prepolymer was formed by heating the mixture at 120° C. for 3 hours under nitrogen at 1 atmosphere while allowing the formed ethanol to distill, followed by heating at 160° C. for 2 hours. The prepolymer was then heated in vacuo (0.05 mm Hg) at 220° C. for 1 hour, and the postpolymerization completed by heating at 215° C. for an additional 6 hours. The polymer was then allowed to cool to room temperature, isolated and ground, and finally dried in vacuo at room temperature.

Polymer Characterization $\eta$inh in $CHCl_3$ = 0.50
DSC (20° C./min): $T_m$ = 210° C.

Polymer Melt Spinning: The polymer was spun using an Instron Rheometer with a 30 mil die at 207° C.

In Vitro Evaluation: The undrawn fibers lost 21 and 66 percent of their initial mass after immersion in phosphate buffer at 37° C. and 42 and 127 days, respectively.

EXAMPLE II

80/20 Poly(1,4-cyclohexylenedicarbinyl-cohexamethylene oxalate)

Distilled diethyl oxalate (43.8 g, 0.300 mole), recrystallized trans 1,4-cyclohexanedimethanol (cis isomer content = 1.0 percent, 36.3 g, 0.252 mole), 1,6-hexanediol (7.4 g, 0.063 mole), and stannous oxalate (12.4 mg, 0.060 mmole) were added under dry and oxygen-free conditions to a glass reactor equipped for mechanical stirring. The prepolymer was formed by heating the mixture at 120° C. for 2 hours under nitrogen at 1 atmosphere while allowing the formed ethanol to distill, followed by 160° C. for 2.5 hours. The mixture was allowed to cool, then reheated in vacuo (0.1 mm Hg) to 140° C. and maintained until the prepolymer melted. The temperature was then increased to 190° C., maintained for 30 minutes, then raised to 200° C. for 1.5 hours. The melt postpolymerization of the stirred polymer was completed by heating at 220° C. for 4.5 hours. The polymer was cooled, isolated, ground (screen size = 2 mm) and dried in vacuo at room temperature. To obtain the final product, the ground polymer was postpolymerized in the solid state in a glass reactor equipped for magnetic stirring by heating at 180° C. in vacuo (0.05 mm Hg) for 24 hours while allowing the formed diols to distill.

Polymer Characterization $\eta$inh in $CHCl_3$ = 1.33
DSC (20° C./min): $T_m$ = 205° C.

Polymer Melt-Spinning: The polymer was spun at 240° C. using an Instron Rheometer equipped with a 40 mil die.

In Vivo Evaluation: Drawn fibers having a diameter of 9 mil were implanted into the gluteal muscles of rats to determine tissue response and absorption characteristics. The median tissue response elicited by the samples was in the slight range after 5 days postimplantation and in the minimal range after 42 days; absorption of the samples was first noted at 120 days and by 180 days approximately 50 percent of the material had been absorbed.

EXAMPLE III

50/50 Poly(trans 1,4-cyclohexylenedicarbinyl-cohexamethylene oxalate)

Distilled diethyl oxalate (38.0 g, 0.260 mole), recrystallized trans 1,4-cyclohexanedimethanol (20.2 g, 0.140 mole), 1,6-hexanediol (16.5 g, 0.140 mole), and stannous octoate (0.33 M in toluene, 0.16 ml, 0.053 mmole) were added under dry and oxygen-free conditions to a mechanically stirred glass reactor. Under nitrogen at 1 atmosphere, the mixture was heated to and maintained at 120° C. for 20 hours, while allowing the formed ethanol to distill. The prepolymer was cooled and then reheated in vacuo (0.05 mm Hg) to and maintained at 80°, 120°, 140°, 165°, 175°, 185°, and 195° C. for 1, 1, 3, 3.5, 2, 1, and 1 hour, respectively. The removal of the diols was continued by heating at 200° C. for 8 hours to complete the postpolymerization. The polymer was cooled, isolated, ground, and then dried in vacuo at room temperature.

Polymer Characterization $\eta$inh in $CHCl_3$ = 0.36

DSC (20° C./min): $T_m = 138°$ C.

Polymer Melt-Spinning: The polymer was extruded at 136° C. using an Instron Rheometer (40 mil die) and immediately drawn 5X at 53° C.

In Vivo Evaluation: Sterilized (by γ-radiation) drawn fiber segments (2 centimeters in length) were implanted into the ventral abdominal subcutis for study of the rate of absorption and tissue reaction. At one week the implants were fragmented, clumping, and migrating, with the bulk of the suture being absorbed between 6 to 11 weeks. Thereafter, fragments were observed in decreasing amounts until at 36 weeks only a few widely scattered particles were noted.

Only mild foreign body reactions were observed to be elicited by the sterilized drawn fiber segments during the test intervals of 3, 14, 28, 48, 90, and 180 days post-implantation.

In Vitro Evaluation: Undrawn fibers exhibited a 57 percent decrease in their initial mass after immersion in phosphate buffer at 37° C. for 28 days.

EXAMPLE IV

30/70 Poly(trans 1,4-cyclohexylenedicarbinyl-cohexamethylene oxalate)

Distilled diethyl oxalate (36.5 g, 0.250 mole), recrystallized trans 1,4-cyclohexanedimethanol (11.5 g, 0.0797 mole), 1,6-hexanediol (22.4 g, 0.190 mole), and stannous octoate (0.33 M in toluene; 0.16 ml, 0.053 mmole) were added under dry and oxygen-free conditions to a mechanically stirred reactor. The mixture was heated to and maintained at 125°, 140° and 160° C. for 2, 2, and 1 hour, respectively, under nitrogen at 1 atmosphere while allowing the formed ethanol to distill. The prepolymer was cooled and then reheated in vacuo (0.1 mm Hg) and maintained at 150° and 185° C. for 16 and 3 hours, respectively. The postpolymerization was completed by maintaining the polymer at 200° C. for 5.5 hours while continuing to remove the diols under vacuum. The polymer was then cooled, isolated, ground and dried in vacuo at room temperature.

Polymer Characterization $\eta$inh in $CHCl_3 = 0.82$
DSC (20° C./min): $T_m = 85°$ C.

Polymer Melt-Spinning: The polymer was extruded at 125° C. using an Instron Rheometer with a 40 mil die. The fiber was drawn 5.6X and annealed at 55° C.

In Vivo Evaluation: Sterilized fibers were implanted into the gluteal muscles of rats to determine their absorption and tissue response characteristics. After 42 days, there was not evidence of any morphologic changes of the implant sites indicating absorption. After 150 days, approximately 2 percent of the fiber cross-sectional area remained.

Foreign body tissue responses to the samples were in the slight range at 5, 21 and 42 day periods and in the minimal range at the 150-day period.

In Vitro Evaluation: Drawn fibers experienced a 100 percent decrease in initial mass after 141 days of immersion in phosphate buffer at 37° C.

EXAMPLE V

5/95 Poly(trans 1,4-cyclohexylenedicarbinyl-cohexamethylene oxalate)

Distilled diethyl oxalate (19.0 g, 0.130 mole), recrystallized trans 1,4-cyclohexanedimethanol (1.0 g, 0.0069 mole), 1,6-hexanediol (16.3 g, 0.138 mole), and stannous octoate (0.33 M in toluene; 0.08 ml, 0.026 mmole) were added under dry and oxygen-free conditions to a glass reactor equipped for magnetic stirring. The prepolymer was formed by heating the mixture at 120° C. for 3 hours under nitrogen at 1 atmosphere while allowing the formed ethanol to distill, followed by 160° C. for 2 hours. The prepolymer was heated and maintained at 205° C. for 8 hours in vacuo (0.05 mm Hg). The polymer was then cooled, isolated, ground, and dried at room temperature.

Polymer Characterization $\eta$inh in $CHCl_3 = 0.88$
DSC (20° C./min): $T_m = 69°$ C.

Polymer Melt-Spinning: The polymer was spun in an Instron Rheometer using a 30 mil die at 85° C. The fibers were drawn 5X at room temperature.

In Vitro Evaluation: The drawn fibers exhibited a 93 percent decrease in their initial mass after immersion in phosphate buffer at 37° C. for 42 days.

EXAMPLE VI

58/42 Poly(1,4-phenylenedicarbinyl-cohexamethylene oxalate)

Diethyl oxalate (14.6 g, 0.100 mole), recrystallized 1,4-benzenedimethanol (6.9 g, 0.050 mole), 1,6-hexanediol 8.3 g, 0.070 mole), and Tyzor TOT* catalyst (0.4 ml of a 1 percent solution) were added under dry and oxygen-free conditions to a glass reactor equipped for stirring. The prepolymer was formed by heating under nitrogen at 1 atmosphere at 140° C. for 4 hours while allowing the formed ethanol to distill. The mixture was then heated in vacuo (0.1 mm Hg) at 165° C. for 22 hours while continuing to remove distillates. A postpolymerization was conducted at 180°, 190°, and 200° C. for 2, 1, and 4 hours, respectively. The polymer was cooled, ground and dried.

*Tyzor TOT, a tetraalkyl titanate catalyst manufactured by E. I. duPont de Nemours & Co., Wilmington, DE 19898.

Polymer Characterization $\eta$inh in HFIP = 0.48
DSC (10° C./min): $T_m = 170°$ C.

In Vitro Evaluation: Immersion of a molded disc, 2.2 cm in diameter and 0.32 cm thick for 8 and 78 days in phosphate buffer at 37° C. resulted in a loss of 3 and 97 percent of the initial mass, respectively.

EXAMPLE VII

56/44 Poly(1,4-phenylenedicarbinyl-cohexamethylene oxalate)

Dibutyl oxalate (20.2 g, 0.100 mole), 1,4-benzenedimethanol (8.3 g, 0.060 mole), 1,6-hexanediol (5.6 g, 0.047 mole), and tetraisopropylorthotitanate catalyst (0.3 ml, of a 0.01 M solution) were added under dry and oxygen-free conditions to a glass reactor equipped for magnetic stirring. The prepolymer was formed by heating at 140° and 160° C. for 1 and 17 hours, respectively, under nitrogen at 1 atmosphere while allowing the formed butanol to distill. The pressure was reduced (0.2 mm Hg) while continuing to heat at 160° C. for an additional hour. The postpolymerization of the polymer melt was completed by heating at 180° and 200° C. for 2 and 3.5 hours, respectively, while continuing to remove distillates. The polymer was cooled, and isolated.

Polymer Characterization $\eta$inh in HFIP = 0.42

DSC (10° C./min): $T_m = 165°$ C.
TGA (10° C./min in $N_2$): Less than 1 percent cumulative weight loss experienced at 250° C.
In Vitro Evaluation: Immersion of a molded disc, 2.2 cm in diameter and 0.22 thick for 7 and 77 days, in phosphate buffer at 37° C. resulted in a loss of 3 and 56 percent, respectively, of the initial mass.

EXAMPLE VIII

50/50 Poly(1,4-phenylenedicarbinyl-cohexamethylene oxalate)

In a manner similar to that employed in Examples X and XI, the above-identified copolymer having the following characteristics was produced:
DSC (10° C./min): $T_m = 175°$ C.
TGA (10° C./min in $N_2$): Less than 1 percent cumulative weight loss experienced at 250° C.
In Vitro Evaluation: Immersion of a molded disc, 2.2 cm in diameter and 0.28 cm thick for 8 and 78 days in phosphate buffer at 37° C. resulted in a loss of 6 and 54 percent of the initial mass, respectively.

Preparation and Administration of Polymer-Drug Compositions

The drug and the polymer can be mixed, and the intimacy of mixing particle size and particle shape of the formulation can be varied by any of a number of known methods. Intimacy of mixing particle size and particle shape of the formulations of the invention will depend to some extent on the intended use. High homogeneity can be obtained by mixing the components in the molten state, cooling, and grinding the resulting solid. A formulation so obtained is suitable for injection as 0.1μ to 1000μ particles suspended in saline solution or a pharmaceutically acceptable oil. In some cases particles with cores of pure drug coated with various thicknesses of polymer can be preferred for delayed and/or sustained release. Relatively large pellets (1–10 mm) may be preferred for reversible implantation in animals by surgery or by injection as projectiles. For this use adequate homogeneity can usually be realized by grinding or milling the drug and the polymer together before forming pellets under pressure. Known techniques of encapsulation, including microencapsulation, can be used to mix the polymer and the drug. The formulations of this invention provide a slow, steady release of drug in contradistinction to conventional preparations which generally produce a rapid surge followed by a fairly quick decline in drug effect.

Polymer-drug mixtures of the invention may contain pharmaceutically acceptable inert additives such as plasticizers. Typical plasticizers are Carbowax polyethylene glycols, glycerides and ethylcellulose.

The relative proportions of the drug and copolyoxalate polymer can be varied over a wide range depending on the desired effect. Since the drug will be released over an extended period of time, the quantity of drug may be greater than the conventional single dose and the polymer must not break down or become absorbed by the body so rapidly as to release undue quantities of drug. The polymer-drug composition may range from 1 percent of drug and 99 percent of the polymer to 99 percent of drug and 1 percent of the polymer. Preferred compositions include 1 part of drug and from 4 to 20 parts of polymer.

These formulations can be injected as fluid suspensions by syringe into subcutaneous cellular tissue or muscular tissue, or implanted in pellet form subcutaneously or intramuscularly. Liquid vehicles useful for suspensions of the drug-polymer formulation include water or aqueous solutions such as normal sodium chloride solution or sodium carboxymethyl cellulose in water. Oils such as sesame oil or peanut oil containing, if desired, dissolved adjuvants such as benzyl alcohol, may also be used to prepare suspensions of the polymer-drug formulation.

Drug compounds of the classes mentioned earlier may be coated, embedded, or intimately mixed in or with a matrix of one or a combination of different chain-length biodegradable polymers to give a drug-polymer mixture which will provide a controlled sustained release of the drug compound over a period of 8 hours to 2 months or longer when administered parenterally.

Coating, embedding or intimately mixing the drug compound with the polymer can be accomplished in the following ways:

(A) Coating the discrete drug particles or drug-particle aggregates, agglomerates or flocs by (1) Spray drying: Finely divided drug particles are suspended in a solvent system in which the drug is not soluble containing the dissolved polymer and other agents, e.g., extenders, plasticizers, dyes, etc., in the drug/polymer ratio from 1/99 to 99/1, followed by spray drying. For example: Drug particles 0.2 to 10 microns in size and equal to the weight of polymer used are suspended in a solvent solution of polymer in such a concentration so as to give a liquid viscosity suitable for atomizing. The drug-polymer mixture is spray-dried using conventional methods of atomizing, e.g., centrifugal wheel, pressure, and two-fluid nozzle using appropriate drying conditions and temperatures that do not exceed the softening point of the polymer and do not exceed the melting point or decomposition point of the drug. Solvents useful in preparing solutions of the polymers of the present invention include, but are not limited to, hexafluoroisopropyl alcohol, hexafluoroacetone, trichloroethane, tetrachloroethane, trifluoroacetone, toluene, dichloroethane, chloroform, and methylene chloride.

(2) Pan coating or fluid-bed coating: Place granules or pellets, 5 microns to 2 mm, preferably between 0.25 and 10 mm diameter, in a rotating coating pan or fluid-bed drier, and apply polymer (dissolved in a carrier to a suitable viscosity for spraying) by spraying until a suitable coating quantity has been deposited to give the required release-rate characteristics. For example: Granules of drug are prepared by extrusion of a wet granulation, or other suitable methods known to the art, and dried. Sixteen to forty mesh granules are placed in a rotating coating pan and a solution of polymer, dissolved in a suitable nonaqueous volatile solvent, is sprayed onto the moving granules with a continuous fine spray under conditions known to the art, until a coating giving the desired release rate has been applied. The granules are then dried.

(3) Microencapsulation: Suspend drug particles, granules or pellets (0.1 to 2000 microns diameter) in a solvent system in which the drug is not soluble, and which contains the polymer in solution. Add an agent incompatible with the polymer-solvent system, such as an incompatible polymer, a nonsolvent for the polymer, or a salt, or vary conditions such as temperature and pressure. One or a combination of the above will precipitate the polymer, coating the drug particles, granules or pellets. For example: 0.5 to 25 micron drug particles are suspended in a low viscosity solution of the polymer in a suitable solvent in which the drug is not soluble. A miscible solvent in which the polymer is not soluble, such as hexane, is then added slowly to precipitate the polymer. The coated particles are filtered and washed with hexane and allowed to dry. The powder is stored for use in the suitable dosage form.

(B) Embedding

The polymer or polymer mixture is melted and a nonheatlabile drug is suspended and thoroughly dispersed in the melt. The melt is congealed by spraying, or in a mass and ground into small particles to give a polymer matrix with the drug embedded. For example: the copolyoxalate polymer is melted and 0.5 to 400 micron (preferably 0.5 to 25 micron) drug particles are suspended and thoroughly dispersed in the molten polymer in a concentration necessary to give the desired release rate patterns. The polymer is solidified by cooling and ground into small pieces 1 to 200 microns in size.

(C) Intimate mixing

The drug and polymer are dissolved in a common solvent and the solvent is removed in some suitable way (spray-drying, flash-evaporation, etc.). For example: the drug and polymer are dissolved in the solvent in a 1:1 ratio and to a concentration of 2 percent. The solvent is flash-evaporated and the resulting film is scraped from the flask and powdered.

The above sustained-release powder, granular or pellet forms may be included in the following type formulations:

(1) Suspensions: Active ingredients of low solubility which have been embedded in or coated with the polymer and are in a finely divided state, 200 microns diameter or less, preferably 50 microns or less, may be suspended in a suitable pharmaceutical vehicle for injection. This vehicle may also contain suspending and thickening agents, e.g., methyl cellulose, and preservatives. These ingredients are combined to give a stable suspension which will release the active ingredient over the time period desired.

(2) Emulsions: Active ingredients insoluble in oil in fine powder form, preferably 10 microns or less, are thoroughly dispersed in a suitable oil, which is, in turn, emulsified in an external aqueous phase (oil in water) using suitable emulsifying agents, e.g., triethanolamine oleate, polyoxyethylene sorbitan monoleate, acacia, gelatin, etc. The aqueous phase may also contain agents such as protective colloids and preservatives, formulated to give a stable emulsion which will provide a controlled release of the active ingredient over the time period desired.

(3) Aqueous suspensions: The active ingredient embedded and/or coated with the polymer in a particle size no greater than 200 microns and preferably no greater than 50 microns is suspended in an aqueous solution which may contain thickening agents, e.g., carboxymethylcellulose; preservatives, e.g., phenol; suspending agents, e.g., polyvinylpyrrolidone; surface active agents; buffers and dextrose or saline to adjust for isotonicity.

(4) Nonaqueous suspensions: The active ingredient embedded and/or coated with the polymer in a particle size usually no greater than 200 microns and preferably no greater than 50 microns is suspended in a suitable oil, etc. The suspension may contain preservatives, e.g., chlorbutanol or methylparaben and propylparaben mixtures, and suspending agents such as aluminum monostearate.

In both the aqueous and nonaqueous preparations, the final product is sterilized by heat, radiation, ethylene oxide, or other suitable means prior to use.

The use of absorbable polymer-drug formulations in the controlled administration of fertility control agents over extended periods of time is well-known. U.S. Pat. No. 3,773,919, for example, describes the combination of poly-L-lactide polymers with endocrine agents such as 17β-estradiol; 2α,17α-diethynyl-A-nor-5α-androstane-2β,17β-diol; 17β-estradiol; 6,6-difluoro-17α-ethynyl-17β-hydroxyestr-4-en-3-one; and 17β-hydroxyestr-4-en-3-one adamantane-1'-methanolcarbonate. The copolyoxalate polymers of the present invention are effectively substituted for the poly-L-lactide polymers of U.S. Pat. No. 3,773,919 to obtain an alternative polymer-drug composition of similar effect.

Polymers and polymer-drug compositions of the present invention are adversely affected by moisture and are accordingly preferably prepared and stored in a substantially moisture-free environment and in hermetically sealed packages. Polymers which have been dried under vacuum at elevated temperatures and subsequently stored under vacuum or in a dry nitrogen environment are found to be quite storage stable.

What is claimed is:

1. In a pharmaceutical depot composition for parenteral administration of effective amounts of a drug released slowly over an extended period of time which comprises a combination of
   (a) from 1 percent to 99 percent by weight of composition of a drug in an effective depot amount greater than the single dose amount, and
   (b) a solid, absorbable polymer which is nonreactive toward body tissue and which undergoes biodegradation in the presence of body fluids into products which are metabolized or excreted by the body without adverse body reaction, the improvement comprising employing as said absorbable polymer isomorphic polyoxalate polymers comprising units of cyclic and linear oxalates and having the general formula

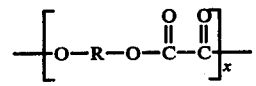

wherein each R is

   I or

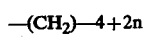   II and from about 5 to 95 mole percent of the R units are I; A is trans 1,4-cyclohexylene or p-phenylene, n is 1 or 2 and is the same for I and II, and x is the degree of polymerization resulting in a polymer having an inherent viscosity of at least 0.20 determined at 25° C. in a 0.1 g/dl solution of polymer in chloroform or hexafluoroisopropanol.

2. The composition of claim 1 wherein n is 1 and A is trans 1,4-cyclohexylene.

3. The composition of claim 1 wherein n is 2 and A is trans 1,4-cyclohexylene.

4. The composition of claim 2 wherein units of formula I comprise from 35 to 80 mole percent of the R groups.

5. The composition of claim 1 wherein n is 1 and A is p-phenylene.

6. The composition of claim 1 wherein n is 2 and A is p-phenylene.

7. The composition of claim 1 wherein the ratio of drug to polymer is from 1:4 to 1:20 by weight.

8. The composition of claim 1 wherein the drug is an endocrine agent.

9. The composition of claim 8 wherein the drug is a fertility control agent.

10. The composition of claim 1 in the form of injectable particles dispersed in normal saline or a pharmaceutically acceptable oil.

11. The composition of claim 10 wherein the injectable particles range in size from about 0.1 to 200 microns.

12. The composition of claim 1 in the form of pellets for implantation.

13. The composition of claim 1 wherein the polymer is a mixture of an isomorphic copolyoxalate and at least one other absorbable polymer.

14. The composition of claim 13 wherein the other absorbable polymer is selected from the group consisting of homopolymers and copolymers of lactide and glycolide.

15. In the process of releasing a controlled effective amount of a parenteral depot drug in an animal or human being over an extended period of time, the improvement comprising administering the composition of claim 1 to said animal or human.

* * * * *